United States Patent [19]

Hartstone

[11] Patent Number: 5,176,035
[45] Date of Patent: Jan. 5, 1993

[54] METERING ARRANGEMENT

[75] Inventor: John L. Hartstone, Auckland, New Zealand

[73] Assignee: Tru-Test Corporation Limited, New Zealand

[21] Appl. No.: 789,421

[22] Filed: Nov. 4, 1991

[51] Int. Cl.⁵ .............................................. G01N 1/00
[52] U.S. Cl. ................................ 73/863.57; 73/864.33
[58] Field of Search ........... 73/863.41, 863.42, 863.43, 73/863.51, 863.52, 863.57, 863.58, 863.81, 863.86, 864.73, 863.61, 864.33; 251/8, 331

[56] References Cited

U.S. PATENT DOCUMENTS

| 34,419 | 2/1862 | Fuller | 251/8 |
|---|---|---|---|
| 2,322,018 | 6/1943 | Huber | 73/863.61 |
| 2,481,882 | 9/1949 | Sebald et al. | 73/863.72 |
| 2,608,866 | 9/1952 | Breedlove et al. | 73/863.61 |
| 3,163,047 | 12/1964 | Jaquith | 73/863.43 |
| 3,308,669 | 3/1967 | Grise et al. | 73/863.57 |
| 3,597,978 | 8/1971 | Siciari | 73/863.86 |
| 3,600,944 | 8/1971 | Hutchings | 73/863.51 |
| 4,580,452 | 4/1986 | Masson | 73/863.86 |
| 4,596,268 | 6/1986 | Jonas | 251/331 |

Primary Examiner—Robert Raevis
Attorney, Agent, or Firm—Ladas & Parry

[57] ABSTRACT

This invention relates to a sub-sampler for obtaining a sample of liquid from a liquid flow, including a housing, liquid inlet and outlet means, a liquid flow line extending therebetween and through said housing, and a chamber on one side thereof, adapted so as to releasably engage a sample vial or container; within said liquid flow line and said chamber are connected so as to allow for flow of liquid therebetween and said liquid flow line is provided with means so as to allow a predetermined portion of liquid passing through said liquid flow line to be diverted into said sample vial or container.

4 Claims, 5 Drawing Sheets

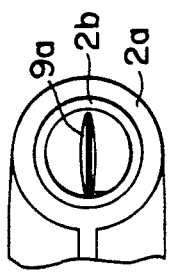
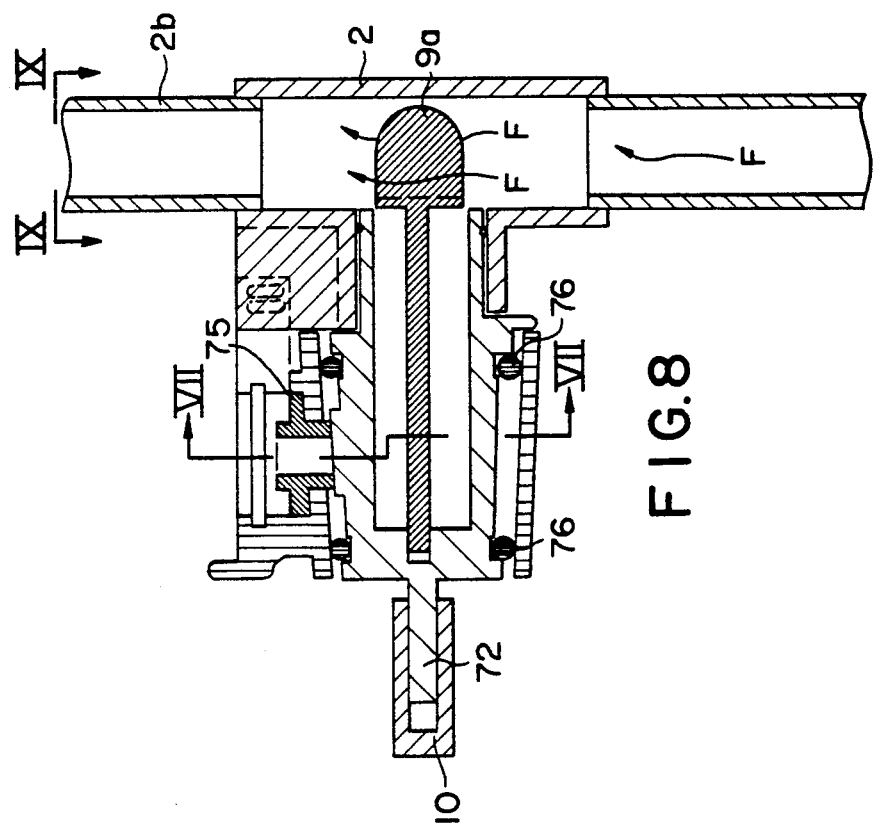
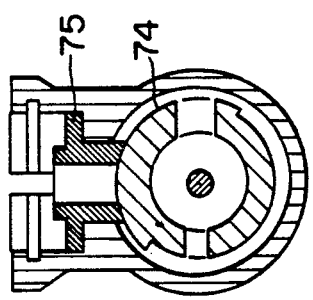

METERING ARRANGEMENT

This application is a continuation of application Ser. No. 556,554, filed Jul 20, 1990, now abandoned, which is a divisional application of my previous U.S. application Ser. No. 388,631 which, now granted as U.S. Pat. No. 4,966,198, is a divisional and continuation-in-part application of my previous U.S. patent application Ser. No. 822,457 filed Jul. 8, 1986, now abandoned, which is a continuation application of my previous U.S. patent application Ser. No. 732,511 filed May 9, 1985, now abandoned, for a Metering Arrangement, now abandoned.

This invention relates to a sub-sampler for use in obtaining a sample of a liquid from a liquid flow.

It has been known up until this time, to provide liquid metering means in association with milking machines and milking arrangements by which mil is drawn from cows. Up until this time, cups of milking machines are placed over the teats of the cow, and vacuum applied, so that the milk is automatically transferred from the teats of the cows, through appropriate feedlines and the like, to milk supply means. In most countries throughout the world, it is necessary that samples of the milk be continuously taken, for the purposes of maintaining standards, checking hygiene, and generally maintaining and metering required standards. For this purpose, metering means have been provided for obtaining a sample of milk passing from cows to a milk storage tank, and samples obtained thereby are passed into an appropriate container or vial for subsequent testing. It will be appreciated that it is always highly desirable that the sample obtained is at least reasonably representative of and proportional relative to, the supply of milk being obtained from the cow.

By way of example, such a metering arrangement is disclosed in U.S. Pat. No. 3,349,617.

While the arrangement disclosed in U.S. Pat. No. 3,349,617 has proven to be particularly satisfactory and commercially successful, it is desirable to provide additions, alternatives and modifications thereto, especially having regard to the requirements of he dairy industry and various governmental authorities throughout the world, in relation to milk testing, sample testing and the like.

While the subject matter of the present application is described by way of example only, with reference to use with a metering arrangement such as that disclosed in U.S. Pat. No. 3,349,617 it should be appreciated that this is by way of example only. In addition, while the specification is described by way of example only, with reference to obtaining milk samples, it should be appreciated that the present subject matter could be used for obtaining samples of any other desired liquid.

In such metering arrangements it is necessary to maintain the highest possible levels of hygiene in order to avoid problems with bacterial build-up and contamination of the milk or infection of the cows. To that end the metering components need to be kept clean and instead of having to dismantle the metering arrangement for such cleaning the present invention has provided a diversion valve which enables "cleaning-in-place" to be effected.

BRIEF SUMMARY OF THE PRESENT INVENTION

The present provides a sub-sampler for obtaining a sample of liquid from a liquid flow, including a housing, liquid inlet and outlet means, a liquid flow line extending therebetween and through said housing, and a chamber on one side thereof, adapted so as to releasably engage a sample vial or container; wherein said liquid flow line and said chamber are connected so as to allow for flow of liquid therebetween, and said liquid flow line is provided with means so as to allow a predetermined portion of liquid passing through said liquid flow line to be diverted into said sample vial or container.

BRIEF DESCRIPTION OF THE DRAWINGS

The present invention will now be described by way of example only and with reference to the accompanying drawings wherein:

FIG. 7 shows a view along arrows VII—VII of FIG. 8.

FIG. 8 shows a side cross-sectional view of the diversionary valve of FIG. 3 when assembled and in its open position.

FIG. 9 shows a view along arrows IX—IX of FIG. 8.

DETAILED DESCRIPTION OF THE PREFERRED EMBODIMENTS OF THE PRESENT INVENTION

Figure 1:
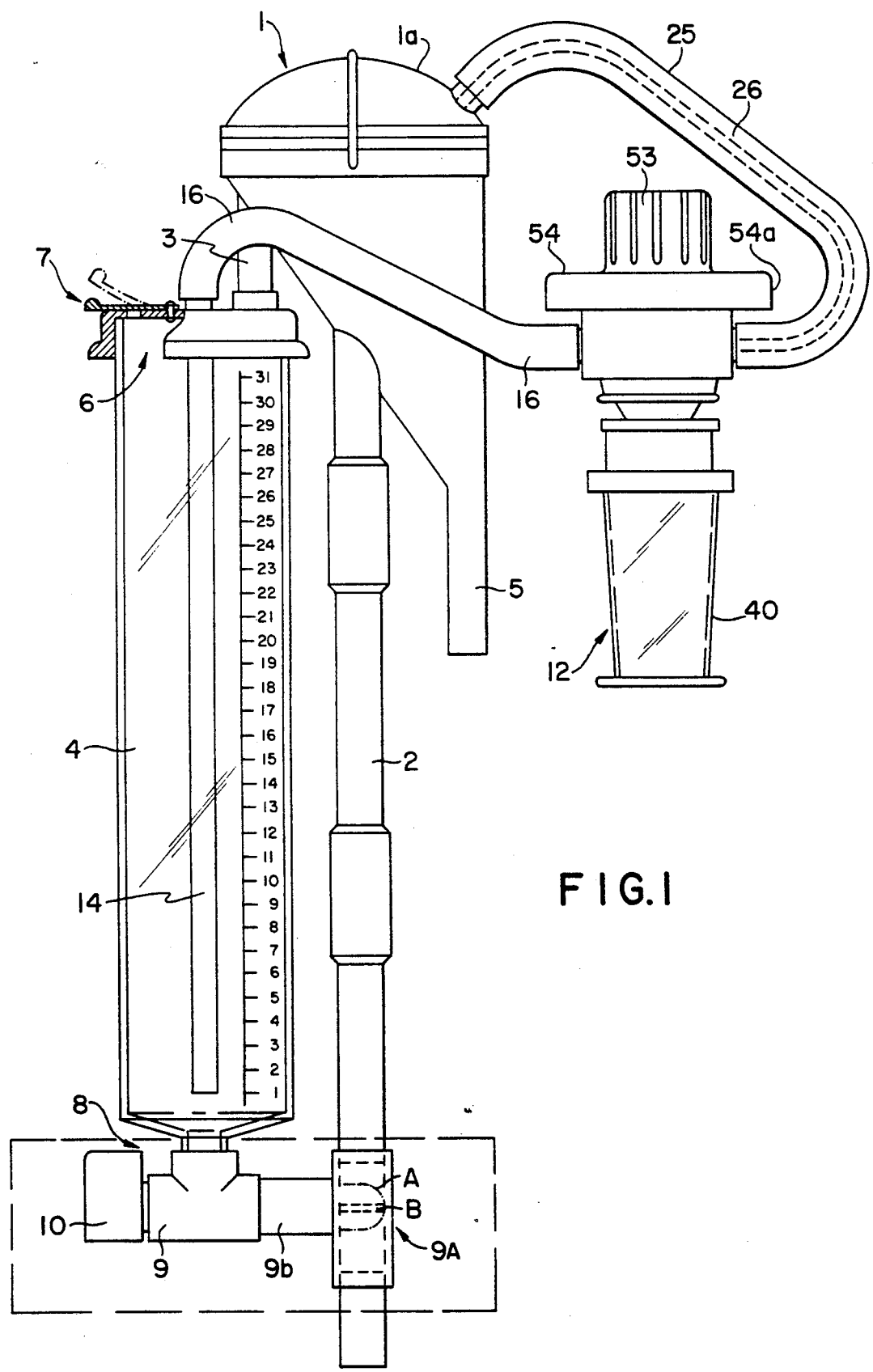
FIG. 1 is a general view of a metering arrangement for use with the sub-sampler of the present invention.

We refer firstly to FIG. 1 of the accompanying drawings.

As discussed above, problems have been encountered previously with obtaining a truly composite sub-sample from previously available milk metering arrangements. When milking a cow or other suitable animal, the initial milk obtained is generally low in butter-fat content, whereas the final milk taken from the cow is generally relatively high in butter-fat content. Thus, milk retained in a sample chamber at the end of milking is generally stratified, with the milk containing a low butter-fat content at the bottom of the sample, but with progressively increasing butter-fat content toward the top of the sample.

The obtaining of a representative sample has previously required pre-stirring of the sample from which the sub-sample id drawn. This has previously been attempted by methods such as for example the introduction o fair to cause turbulence as a stirring medium.

However, the metering arrangement in a preferred embodiment of the present invention allows for a representative sample to be obtained, without the requirement of pre-stirring or the like. The present invention allows for a predetermined portion of the milk taken from an animal to enter the sample chamber. A predetermined portion of the liquid in the sample chamber is then passed into the sample chamber continuously, during the transfer of the original sample back to the main volume of milk taken from the animal. Because the transfer of the liquid to the sample chamber is constant throughout the milking process, the retained sub-sample is representative of the total sample when mixed thoroughly.

Thus, it should be appreciated that a predetermined portion of all the milk obtained from an animal is diverted into the sample chamber of a metering arrangement according to the present invention. Thereafter, a predetermined and constant portion of the sample of liquid within the sample chamber is diverted into the sample vial or container. Thus, the sub-sample contained within the vial or sub-sample container is in fact obtained from continuous sampling of the entire milk or liquid obtained from the cow or other animal, and thus is representative of the entire milk taken from the cow during that milking session. It should also be appreciated that the portion of liquid directed to the sub-sample container or vial can be infinitely varied and calibrated, as will be further described hereinafter.

Referring firstly to FIG. 1 of the accompanying drawings, a milk inlet line 2 is provided leading into a liquid meter 1 leading from the milking cups associated with milking machinery (not shown), which draw milk from a cow.

Milk is drawn into the liquid meter 1 by a vacuum and a proportion of the milk passes from the liquid meter 1 through a transfer means, connection tube or bore 3, and into a sampling chamber 4. A valve (not shown), such as for example in flap valve, is provided at the connection between the outlet passage 3 and the chamber 4. The chamber 4 is under vacuum, causing the flap valve to open and milk to enter the chamber 4. The remainder of the milk from the meter 1 exits through the outlet 5 into appropriate milk collection or storage means (not shown).

The chamber 4 is preferably in the form of an elongate container or tubular vial, which is provided with appropriate markings or calibrations on the exterior thereof, so that a clear indication can be obtained as to the amount of liquid therein. Preferably the chamber 4 is constructed of an at least substantially transparent plastic or glass material. Other materials can however be used.

At the upper end of the chamber 4 is an air inlet 6. This can be in the form of one or more holes or bores covered by an approximate cover or valve 7. The valve 7 may be a flat or plate valve (for example of a flexible and/or resilient material), which is preferably biased into a closed position against the inlet 6. If however it is desired to allow for the entry of air (as will be described hereinafter), the valve 7 is merely lifted against its natural bias, to allow for the entry of such air. It should be appreciated that any form of the appropriate valving can be used.

At the lower end of the main chamber 4 there is provided an outlet 8 which is in turn provided with valving 9, according to the present invention which is described in greater detail hereinafter with reference to FIGS. 3 to 9.

The milk inlet line 2 and the main chamber 4 are connected one to the other through the valving 9. The valving 9 includes a tubular connection 9b linking the milk inlet 2 and the chamber 4.

The particular advantage of this connection and valving (to be described further hereinafter) is that it allows cleaning of the equipment in a particularly efficient and straight forward manner as compared with the methods of cleaning used up until this time. In particular it allows for what is commonly know as "CP", that is; cleaning in place.

Up until this time, when milking had finished and it was desired to clean the equipment (for example with water or water and a suitable surfactant or cleaning material) it was necessary to change around the equipment to allow for a counter-flow against that which normally occurred. Sometimes it was necessary to disassemble the equipment for satisfactory cleaning. By providing an arrangement according to the present invention, the valving 9 can be operated by movement of the toggle handle 10 which allows for a complete "flow through" of cleaning liquid.

The valving 9 includes an elongate tubular valve body 71 and arm 70 which has a basically flap valve 9a at the end thereof. The flap valve 9a extends into, and is capable of controlling flow through, the inlet pipe 2. On actuation of the toggle 10, valve 9a can be moved between positions 'A' and 'B'. As shown in position "A" in FIG. 1, the flap valve 9a is in a substantially vertical or upright position and it does not obstruct (or provides minimal obstruction to) the flow of milk through the inlet line 2. At this position, as will be described below, the liquid-flow path between the valving 9 and the main chamber 4 is closed. Actuation of the toggle 10 into its other position turned through 90° will turn the flap valve 9a into the position shown at 'B'. Here, the flap valve 9a is diverting a substantial portion of liquid through the valve 9 and into the chamber 4.

In this position 'A', the flap valve 9a is in a substantially horizontal or flat position (in which it is substantially transverse to the longitudinal axis of the inlet line 2) and in which it at least partially obstructs the flow of liquid through the milk line 2.

When milking is in progress, the toggle 10 and valve 9 are actuated to that valving between the chamber 4 and the valve 9 is closed, and so the flap valve 9a is essentially in the position "A". This closes the valving between the main chamber 4 and the valve 9 (and indeed the milk line 2) so that the milk flows through the milk line 2 and into the metering device 1. Once milking has ceased, and it is desired to carry out cleaning, appropriate connections are made to allow for the flow of water and/or a surfactant and cleaning liquid through the inlet line 2. The toggle 10 and valve 9 are then moved into position 'B' in which the flap valve 9a is in substantially transverse position substantially shown as "B" in FIG. 1 of the drawings. The movement of the toggle 10 also opens the valving between the main chamber 4 and 9, and connects also the milk line 2 to the main chamber 4.

At the new location of the flap valve 9a, the flow of liquid through the milk line 2 will be substantially diverted through the valving 9 and up into the chamber 4. At the same time however, due to the slightly smaller size of the flap valve 9a relative to the internal bore of the milk line 2, and possibly a certain flexibility or resilience of the flap valve 9a, a proportion of the liquid will also be caused to pass up the milk line 2 thus allowing for a "flow through" of cleaning liquid to allow for complete cleaning in place.

By way of example only, in position 'B' of the flap valve 9a, between about 60% and 80% of the cleaning liquid can pass through the valve 9 into the chamber 4, whereas, about 20% to 40% can pass up the inlet line 2.

If desired, the valving 9 can be provided with a number of different positions, allowing for differing rates of flow through inlet line 2 and/or into the main chamber 4.

Figure 3:
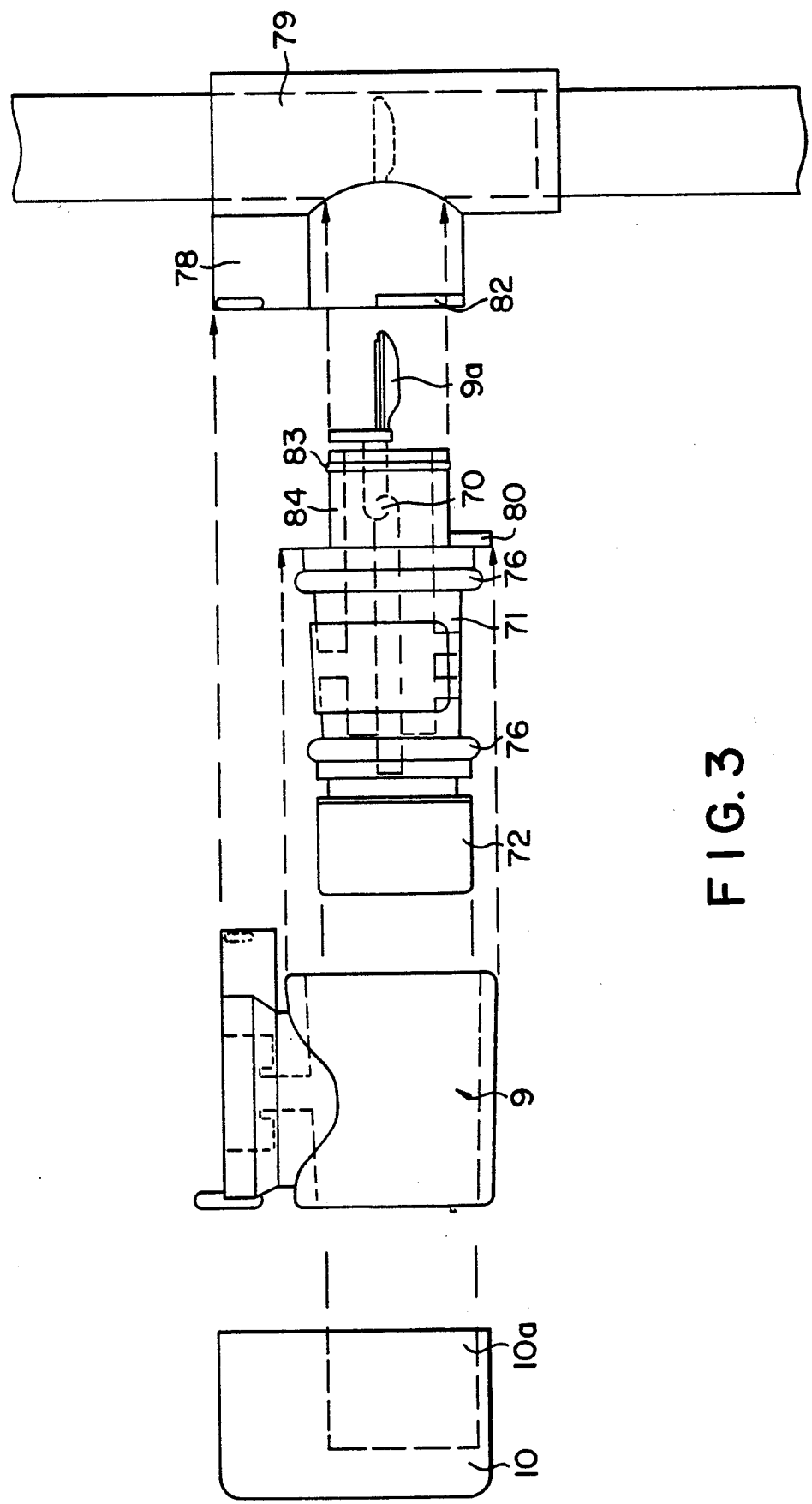
FIG. 3 shows an exploded view of the diversion valve within the area indicated in outline in FIG. 1 and in its diversionary position.

Referring to FIG. 3 of the accompanying drawings the valve 9 is shown with the toggle 10 substantially vertical with the flap valve 9a substantially horizontal. The flap valve 9s is shown provided at the end of an arm 70 extending through the body 71 of the valve 9 to a flange 82 which fits within a recess 10A of toggle 10.

Figure 6:
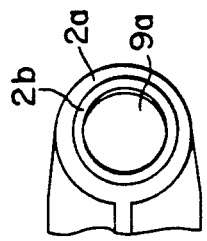
FIG. 6 shows a view along arrows VI—VI of FIG. 5
Figure 5:
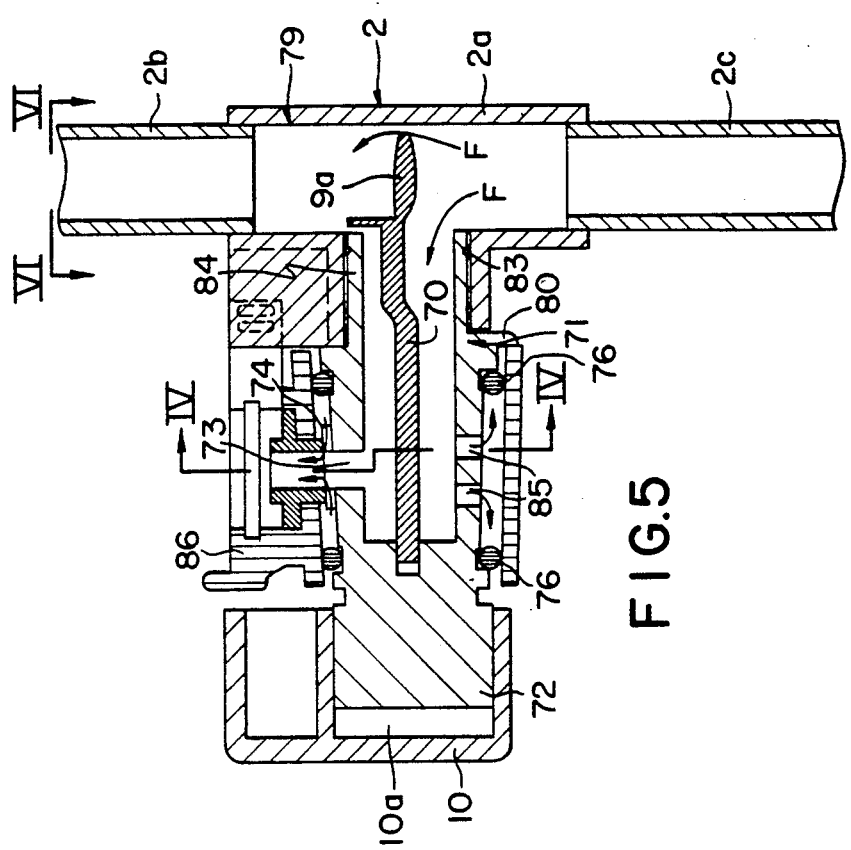
FIG. 5 shows a cross-sectional side view of the diversion valve of FIG. 3 when assembled and in its diversionary position.

Referring particularly to FIGS. 3, 5 and 6, it is seen that in the position of the flap valve 9a as shown in those figures, a slight gap exists between the edge of the flap valve 9a and the internal bore of the flow line member 2A. The flow line 2 is shown as comprising a tubular body portion 2a into which tubular line members 2b and 2c are able to fit. As illustrated in FIG. 5 by arrows 'F', the cleaning liquid flowing upwardly through the tube 2c into the tubular member 2a is substantially diverted by the flap valve 9a in the position shown in FIG. 5, so as to flow into the valve body 71. Here the liquid will pass through the substantially hollow body and exit downwardly through a pair of ports 85 and upwardly through an exit port 73.

Figure 4:
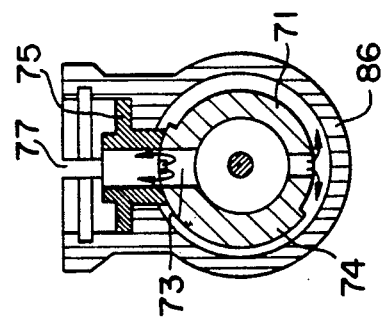
FIG. 4 shows a view along arrows IV—IV of FIG. 5.

A raised portion 74 provided on either side of the exit port 73 slidably engages with a grommet 75 provided in the valve port in housing 86 to provide a seal thereagainst, as liquid flows therethrough into the chamber 4 in the position shown in FIGS. 4 and 5 but, (see FIGS. 7 and 8) also provides a seal thereagainst, to prevent flow of liquid therethrough in either direction when the flap valve 9a is in its other position. It is seen that the raised area 74 provides a cam-like or pad surface engaging with the bottom surface of the grommet 75, suitably a plastic or rubber grommet 75, to provide a seal therewith. It will also be appreciated from FIGS. 4 and 5 that the bottom apertures 85 in the valve body 71 provide for a splitting of the liquid flow therethrough so that the cleaning liquid will pass on both sides of the valve body 71 and on either side of the raised surface 74 and along the respective O-ring seals 76, to provide a cleaning of all the surfaces which could be harbouring material build up or bacterial activity.

A slot 77 (see FIG. 4) is shown provided in the valve housing 79 at an upper portion thereof to provide a location for a flange 78 provided on the flap valve housing 79 (see FIG. 3).

The engagement of the slot 77 with the flange 78 serves to maintain the valve housing 79 to stationary. A projection 80 provided for a bottom portion of the valve body 71 is able to slidably engage in a quadrant shaped slot 82, provided for the flap valve housing 79, so as to define the quadrant through which the valve body 71 and the flap valve 9a is able to move. A further O-ring 83 is shown provided for the projecting portion 84 of the valve body 71 so as to provide a seal relative to the liquid line 2.

In FIGS. 7, 8 and 9 the flap valve 9a is shown extending substantially vertically thus providing minimal obstruction to the flow of liquid therepast as indicated by the arrows 'F', while the engagement of the enlarged surface 74 with the sealing grommet 75 prevents flow of liquid into the main chamber 4.

The size and disposition of the apertures 73 and 85 in the valve body 81 may be such as to result in substantially 50% for example of the liquid passing out through the aperture 73 while the remaining 50% divides between the apertures 85.

The provision of the double apertures 85 provides a flow of cleaning liquid on either side of the "sealing pad" or surface 74, to provide for an effective cleaning of all the valve body surfaces and also the internal surfaces of the 'O' rings 76.

It is thus seen that by the use of the diversion valve 9 of the present invention, a speedy and efficient cleaning-in place operation can be effected.

Referring further to FIG. 1 of the accompanying drawings, while the main chamber 4 is receiving a sample of milk from the meter 1, (in turn from the milk line 2) this is often a relatively large amount of milk. However it is often required or desirable to have a smaller but still representative amount for the purpose of sampling. Accordingly, it is advantageous to provide a further sampling arrangement which provides for an effective "sub-sample" from the main chamber 4, but which is still proportional to, and representative of, the milk in the main chamber 4.

For this purpose, a sub-sampler arrangement 12 is provided.

In order to pass the milk from the main chamber 4 into the sub-sample 12, outlet line 14 is provided with the chamber 4, being substantially elongate in formation and extending through a sealed recess in he top of the main chamber 4, thereafter being connected to an inlet line 16 leading to the sampler 12.

The outlet line 14 is elongate and constructed of any appropriate material such as for example stainless steel and is spaced apart from the bottom of the main chamber 14.

Thus, in use, milk is exited from the chamber 4 through the outlet line 14, and through the inlet line 16 which is connected to the inlet 20 of the sub-sampler 12. An outlet line 25 from the sub-sampler 12, leads from the outlet 21 back to the meter 1, to which it is connected and in communication. Preferably, the outlet line 25 connects to an upper portion 1a of the meter 1. This is not however essential.

Thus, when it is desired to obtain a proportional representation of the milk from the main chamber 4, it is necessary to pass the milk in that chamber through and into the sub-sampler 12. The meter 1 is generally under vacuum, and thus, the valve 7 associated with the air inlet 6 is opened or lifted (so as to communicate with atmosphere). This allows air into the main chamber 4 which will in turn draw closed the valve between the entry pipe 3 from the meter 1, and the main chamber 4. The entry of air into the chamber 4 causes milk within the chamber 4 to pass up through the outlet pipe 14, through the inlet line 16 and into the sub-sampler 12.

This then is an efficient and straight forward way of transferring milk from the main chamber 4 into the sub-sampler 12.

Figure 2:
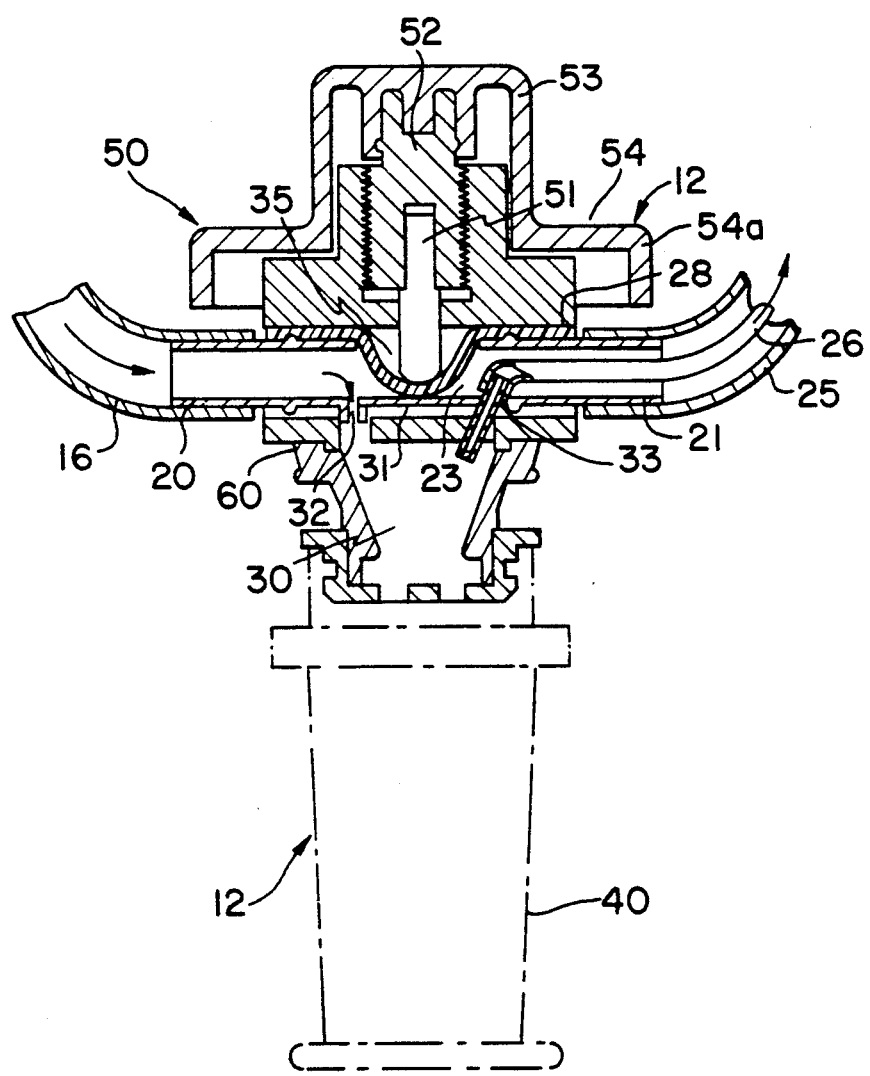
FIG. 2 is a sectional view of a sub-sampler arrangement for use in the metering arrangement of FIG. 1.

Referring now to FIG. 2 of the accompanying drawings, this shows a sectional view of a sub-sampler 12 according to one form of the invention. The sub-sampler 12 has a housing 60 which includes a chamber 30 and a substantially transverse bore 31, through which a liquid flow line 23 (to be described hereinafter) can pass. A liquid inlet 20 extends into the housing and a liquid outlet 21 extends outwardly of the housing.

In use, a liquid inlet line 16 (such as from the chamber 4), is connected to the inlet 20. An elongate outlet line 25 can be attached to the outlet 21, so as for example to extend to a connection with the meter 1. The connection lines 16 and 25 are preferably constructed of a flexible material. This is by way of example only however. The liquid flow line 23 extends between the inlet 20 and the outlet 21 so as to extend through a transverse bore 31 of the housing. Preferably a bore, recess or scallop 35 is formed in an upper surface of the liquid flow line, substantially medially thereof, and an elongate, tubular sleeve 28, of a flexible and/or resilient material is located over and about at least part of the flow line 23 so as to also pass over and about the recess, bore or scallop 35 therein. Annular ribs or ridges can be provided about the outer surface of the flow line 23, so as to hold the flexible and/or resilient sleeve 28 in position.

The housing is provided with the lower chamber 30 which is in communication with the liquid flow line 23. The chamber 30 is substantially hollow, and is provided with means to enable it to releasably locate or engage with a sample vial or container 40, to collect a sample from liquid passing through the sub-sampler 12 (as will be described hereinafter).

One or more holes or connection lines 32 extend from the flow line 23 into the chamber 30. For example in one form of the invention a slot or hole 32 can be provided in the liquid flow line, and a tube engaged therewithin, so that a tubular connection is provided between the liquid flow line 23 and the chamber 30 inwardly of the inlet 20. Preferably, an air outlet 33 is provided extending from the chamber 30 into the liquid flow line 23, spaced inwardly of the outlet 21.

Preferably a tubular connection is provided as will be described hereinafter.

In use thereof, liquid flowing through the liquid flow line 23 (having entered through the inlet line 16) will pass through the liquid flow line 23 and a proportion of the liquid is able to pass into the chamber 30 through the liquid inlet 32. The liquid then passes into the sample vial or container 40 releasably connected to the chamber 30. Excess air carried into the chamber 30 by the liquid, exits through the air outlet 33 as referred to hereinafter.

The sub-sampler 12 provides means for controlling the flow of liquid through the liquid flow line 23, and thus controlling the amount of liquid that passes through the liquid inlet 32, into the chamber 30 and any vial or container releasably engaged therewtih. In the form of the sub-sampler 12 shown in FIG. 2 of the drawings, a control actuating means 50 acts on a restriction member, which is an elongate plunger 51, which is mounted adjacent and above the liquid flow line 23, and in particular immediately above the bore or scallop 35 as covered by the flexible and/or resilient sleeve 28. The plunger 51 is preferably mounted within appropriate mounting and actuating means, and is preferably spring biased by the resilience of the material of the flexible and/or resilient sleeve 28 and into a position away from the liquid flow line 23. In one form of the sub-sampler 12 as shown, the plunger 51 is axially mounted with a boss 52. The boss 52 is engaged with an appropriate actuating means. In the preferred form of the sub-sampler 12 shown in FIG. 2, the actuating means includes an outer cap 53.

Rotation of the cap 53 causes the movement of the boss 52 in its threaded bore and thus the plunger 51 to move axially downwardly, against the bias of the sleeve 28, so as to depress the sleeve 28 extending over the bore or scallop 35.

A continued rotation of the actuating means 50 and downward axial movement of the plunger 51 causes the flexible and/or resilient sleeve 28 to move through the bore or scallop 35 and into the path of the flow line 23, thus restricting the flow of liquid therethrough. Thus, the more the plunger 51 is moved downwardly, the more restricted is the flow of liquid through the flow line 23, and thus the more liquid which is diverted through the liquid inlet 32, into the chamber 30 (and thus into any vial or container 40 releasably engaged therewith). As will be appreciated from FIG. 2 of the drawings, the plunger 51 is shown in a position in which it substantially closes off the flow of liquid through the flow line 23, and thereby diverts a substantial proportion of the liquid through the liquid inlet 32, into chamber 30.

The cap 53 has a radially extending flange 54, having a downwardly depending skirt 54a at its outer periphery.

The outer surface of the skirt 54a can be provided with calibrations or graduations thereon and a central marker or arrow can be provided on the main body portion of the housing in a position substantially intermediate the liquid flow line 23, and substantially aligned with location of said plunger 51.

In use therefore, if it is desired to obtain a sample of liquid proportional to the amount of liquid in the chamber 4, (as shown in FIG. 1 of the accompanying drawings), the actuating means 50 is rotated so that the graduation or calibration 54b on the skirt 54a thereof, as positioned by the pointer or marker on the body of the housing, corresponds to the level of liquid within the chamber (as shown by markings or graduations on the chamber 4). This will then determine the degree to which the flow of the liquid is restricted as it passes through the liquid flow line 23, and thus provides a sample from the chamber 4, which is substantially proportional and representative of the liquid in the chamber 4.

While the invention has been described by way of example only, to the actuating means being in the form of a rotatable control means 50, which causes axial longitudinal movement of the plunger 51, towards and away from the flexible/resilient sleeve 28 passing about the liquid flow line 23, it should be appreciated that other means can be used to move the plunger or some similar mechanism, inwardly and outwardly of the liquid flow line. Also, other means can be provided for restricting the flow of liquid passing through the liquid flow line, such as for example venturi arrangements, variable valving arrangements and the like. The arrangement described with reference to FIG. 2 of the accompanying drawings is by way of example only.

Referring now to the air outlet 33, extending from the chamber 30 into the outlet 21. Preferably an elongate tubular outlet extends from the chamber 30 into the liquid flow line 23, inwardly of the outlet 21.

The air outlet line 33 allows air which passes into the chamber with liquid, to be exited from the chamber 30, as the presence of such air would detract from the efficiency and operation of the invention.

In one form of the invention the air outlet 33 can merely release the air into the liquid flow line 23 and the outlet line 25, where it will join liquid and pass back into the meter 1. In a preferred form of the invention however, as shown in FIGS. 1 and 2 of the accompanying drawings, an elongate tube 26 of relatively small diameter, is connected to the air outlet 33 and passes through the liquid outlet line 25, substantially concentrically, so as to exit also into the meter 1. The air from the air outlet 33 therefore travels separately (from the liquid)

through the liquid outlet 25, to be passed into the meter 1. This has been found to be particularly efficient in use, as it avoids the passage of air directly into the liquid flow line 23 and liquid outlet line 25, which could cause turbulence, back flow, and generally detract from the efficiency of operation.

As indicated hereinbefore, a liquid outlet 25 is connected to the outlet 21 and preferably passes into the meter 1, so that in use the liquid passing through the liquid flow line 23, exits from the outlet 21 then passes through the outlet line 25 back in to the meter 1, where at least the majority thereof will pass through the outlet 5 into an appropriate liquid collection or storage means. It is possible however that some of the liquid might again pass through the meter 1 into the chamber 4 to be recirculated.

It should be appreciated that modifications and improvements may be made to this invention without departing from the scope of or spirit thereof.

I claim:

1. A sub-sampler for obtaining a sample of liquid from a liquid flow, comprising a housing; liquid inlet means and outlet means provided respectively for leading the liquid flow in and out of the housing; a liquid flow line extending therebetween and through said housing; a chamber formed in said housing and on one side of the liquid flow line, said chamber being adapted to be releasably connected with a sample vial or container; an inlet aperture formed on wall defining the liquid flow line and so positioned that the liquid flow line and the chamber are connected by the aperture to allow a predetermined portion of liquid passing through the liquid flow line to enter the chamber thereby to be diverted into the sample vial or container; a flexible and resilient sleeve covering at least part of said liquid flow line and extending over a bore on the liquid flow line and an actuating means downstream of said inlet aperture, said actuating means being an elongated plunger mounted against said sleeve in the bore so that on actuation of said actuating means, the elongate plunger is caused to move toward said sleeve and depress said sleeve to restrict passage of the liquid through the liquid flow line thereby determining the portion of the liquid entering the chamber through the inlet aperture.

2. The sub-sampler of claim 1, wherein an air outlet leads from said chamber into said liquid flow line downstream of said aperture.

3. The sub-sampler of claim 2, wherein said air outlet is connected with a conduit lying longitudinally in said liquid flow line.

4. The sub-sampler of claim 1 wherein said actuating means has mounted thereon control means including a rotatable grip member having a central base portion and a radially extending flange with a peripheral and downwardly extending skirt, said skirt being provided with a plurality of markings or calibrations thereon; at least one marking being provided on the housing of the sub-sampler, at a position substantially aligned with a location of the actuating means so that on rotation of the grip member, the actuating means is moved toward and against the sleeve which is moved inwardly into the liquid flow line.

* * * * *